US010449798B2

(12) United States Patent
Abe et al.

(10) Patent No.: US 10,449,798 B2
(45) Date of Patent: Oct. 22, 2019

(54) SECURITY MARK, AUTHENTICATION METHOD THEREFOR, AUTHENTICATION DEVICE AND MANUFACTURING METHOD AS WELL AS SECURITY MARK INK AND MANUFACTURING METHOD THEREFOR

(71) Applicant: JAPAN SCIENCE AND TECHNOLOGY AGENCY, Kawaguchi-shi, Saitama (JP)

(72) Inventors: Jiro Abe, Sagamihara (JP); Yoichi Kobayashi, Sagamihara (JP)

(73) Assignee: JAPAN SCIENCE AND TECHNOLOGY AGENCY, Kawaguchi-Shi, Saitama (JP)

( * ) Notice: Subject to any disclaimer, the term of this patent is extended or adjusted under 35 U.S.C. 154(b) by 0 days.

(21) Appl. No.: 15/120,488

(22) PCT Filed: Jan. 28, 2015

(86) PCT No.: PCT/JP2015/000371
§ 371 (c)(1),
(2) Date: Aug. 19, 2016

(87) PCT Pub. No.: WO2015/133056
PCT Pub. Date: Sep. 11, 2015

(65) Prior Publication Data
US 2017/0066280 A1    Mar. 9, 2017

(30) Foreign Application Priority Data

Mar. 3, 2014 (JP) ................................ 2014-040378

(51) Int. Cl.
*G01J 1/58* (2006.01)
*B42D 25/387* (2014.01)
(Continued)

(52) U.S. Cl.
CPC ......... *B42D 25/387* (2014.10); *B42D 25/378* (2014.10); *B42D 25/382* (2014.10);
(Continued)

(58) Field of Classification Search
CPC ........... G01N 21/6428; G01N 21/6458; G01N 21/64; G01N 21/6408; G01N 2021/6421
See application file for complete search history.

(56) References Cited

U.S. PATENT DOCUMENTS 5,289,547 A    2/1994 Ligas et al.
5,702,511 A    12/1997 de Saint-Romain et al.
(Continued)

FOREIGN PATENT DOCUMENTS

CN    1097453 A    1/1995
CN    102036992 A    4/2011
(Continued)

OTHER PUBLICATIONS

The International Search Report dated Mar. 17, 2015 in PCT/JP2015/000371 with English translation (8 pages).
(Continued)

*Primary Examiner* — David P Porta
*Assistant Examiner* — Mamadou Faye
(74) *Attorney, Agent, or Firm* — Acuity Law Group, PC; Michael A. Whittaker

(57) ABSTRACT

A method for authenticating a security mark containing a photochromic compound can provide higher security performance. The method comprises a process of irradiating a security mark containing a photochromic compound with excitation light, a process of acquiring first security information on a time-dependent change in the absorption spectrum and/or reflection spectrum of the security mark after the irradiation with excitation light, and a process of checking the acquired first security information against previously
(Continued)

acquired first security information on the security mark. In this method, the security mark preferably contains two or more photochromic compounds different from one another in color development and/or in quenching rate after the color development in a photochromic reaction.

7 Claims, 6 Drawing Sheets

(51) Int. Cl.
*C09D 11/50* (2014.01)
*B42D 25/378* (2014.01)
*B42D 25/382* (2014.01)
*C09K 9/00* (2006.01)
*G01N 21/33* (2006.01)
*G01N 21/64* (2006.01)
*G07D 7/1205* (2016.01)
*C09K 9/02* (2006.01)

(52) U.S. Cl.
CPC ............... *C09D 11/50* (2013.01); *C09K 9/00* (2013.01); *G01N 21/33* (2013.01); *G01N 21/64* (2013.01); *G07D 7/1205* (2017.05); *C09K 9/02* (2013.01)

(56) References Cited

U.S. PATENT DOCUMENTS

| | | | |
|---|---|---|---|
| 2003/0006223 A1* | 1/2003 | Davis | A61B 5/083 219/201 |
| 2004/0023397 A1 | 2/2004 | Vig et al. | |
| 2008/0292828 A1 | 11/2008 | Bott et al. | |
| 2009/0141961 A1 | 6/2009 | Smith et al. | |
| 2011/0060113 A1 | 3/2011 | Gessner et al. | |
| 2011/0127763 A1* | 6/2011 | Benenati | B32B 7/12 283/74 |
| 2011/0157539 A1* | 6/2011 | Rosset | D21H 21/16 349/193 |
| 2011/0306743 A1* | 12/2011 | Abe | C07D 233/58 526/219.6 |
| 2012/0001412 A1 | 1/2012 | Kumaraswamy | |
| 2012/0074682 A1* | 3/2012 | Rosset | B44F 1/08 283/72 |
| 2013/0093174 A1 | 4/2013 | Downing et al. | |
| 2013/0135979 A1 | 5/2013 | Bott et al. | |
| 2013/0305947 A1* | 11/2013 | Iftime | C09D 11/101 101/483 |
| 2014/0106963 A1* | 4/2014 | Ribi | B41M 5/3331 503/216 |
| 2015/0240297 A1* | 8/2015 | Jaime | C12Q 1/68 506/8 |

FOREIGN PATENT DOCUMENTS

| | | |
|---|---|---|
| CN | 102282218 A | 12/2011 |
| JP | 0839611 A | 9/1996 |
| JP | 08239611 A | 9/1996 |
| JP | 08245579 A | 9/1996 |
| JP | 2000112074 A | 4/2000 |
| JP | 2005266608 A | 9/2005 |
| JP | 2005215640 A | 11/2005 |
| JP | 2005325087 A | 11/2005 |
| JP | 200622202 A | 1/2006 |
| JP | 2008505193 A | 2/2008 |
| JP | 2010173292 A | 8/2010 |
| JP | 2011132265 A | 7/2011 |
| JP | 2015501233 A | 1/2015 |
| TW | 200930996 A | 7/2009 |
| WO | 0106453 A1 | 1/2001 |
| WO | 2013054290 A1 | 4/2013 |

OTHER PUBLICATIONS

Hartley, G.S., "The Cis-form of Azobenzene", Nature, 1937, p. 281.
Hayashi and Maeda, "Preparation of a New Phototropic Substance", Bull Chem Soc Jpn, 1960, 33(4):565-566.
Office action issued by SIPO in corresponding Chinese patent application No. 201580011686.7 dated May 12, 2017—incl Engl lang transl.
The Extended European Search Report issued in EP 15758242 dated Oct. 17, 2017.
The Office Action issued by SIPO in Chinese Patent Application No. CN 201580011686.7 dated Jan. 23, 2018—incl Engl lang tranl (10 pages total).
Office Action issued by the JPO in Japanese Patent Application No. 2016-506104 dated Feb. 1, 2019 (4 pages)—incl Engl lang transl.
Office Action issued by TIPO in Tawanese Patent Application No. 104105968 dated Oct. 30, 2018.

\* cited by examiner

SECURITY MARK, AUTHENTICATION METHOD THEREFOR, AUTHENTICATION DEVICE AND MANUFACTURING METHOD AS WELL AS SECURITY MARK INK AND MANUFACTURING METHOD THEREFOR

CROSS-REFERENCE TO RELATED APPLICATIONS

The present invention is filed under 35 U.S.C. § 371 as the U.S. national phase of International Patent Application No. PCT/JP2015/000371, filed 28 Jan. 2015, which designated the U.S. and claims the benefit of priority to Japanese Patent Application No. 2014-040378, filed 3 Mar. 2014, each of which is hereby incorporated in its entirety including all tables, figures and claims.

TECHNICAL FIELD

The present invention relates to a security mark, a method and a device for authenticating the mark, a method for producing the mark, an ink for the security mark, and a method for producing the ink. The invention more specifically relates to, for example, a method for authenticating a security mark containing a photochromic compound.

BACKGROUND ART

Examples of known photochromic compounds showing photochromism include diarylethene (Patent Literature 1), spiropyran (Patent Literature 2), hexaarylbiimidazole (Non Patent Literature 1), and azobenzene (Non Patent Literature 2) compounds. "Photochromism" is also called "photochromy" or "phototropism (phototropy)" and refers to a phenomenon of some types of materials in a solid or solution state changing its color by absorption of light (ultraviolet or visible light) having a specific wavelength and retrieving the original color by absorption of light (ultraviolet or visible light) having another wavelength or by cessation of the absorption of light.

Since the photochromic compounds reversibly develop the colors by absorption of light, they are being studied to be used as a light-modulating material (Patent Literature 3) or an optical recording material (Patent Literatures 4 and 5). Patent Literature 6 describes an ink containing a photochromic compound and having light stability to maintain the color density even after absorption of light for a long time.

Patent Literature 7, which is an application by the present inventors, discloses a security ink containing a photochromic compound. A security ink layer is formed with this security ink by, for example, a coating or printing process. When the security ink layer is irradiated with light, such as ultraviolet light, a security mark such as a character or drawing formed by the coating or printing process becomes visible as a result of color development of the photochromic compound and becomes invisible as a result of color quenching of the photochromic compound by cessation of the irradiation. It should be noted that Patent Literature 7 does not describe any security ink containing two or more compounds having different photochromic characteristics.

CITATION LIST

Patent Literature

Patent Literature 1: Japanese Unexamined Patent Application Publication No. 2005-325087
Patent Literature 2: Japanese Unexamined Patent Application Publication No. 2005-266608
Patent Literature 3: Japanese Unexamined Patent Application Publication No. 2005-215640
Patent Literature 4: Japanese Unexamined Patent Application Publication No. 2000-112074
Patent Literature 5: Japanese Unexamined Patent Application Publication No. H08-245579
Patent Literature 6: Japanese Unexamined Patent Application Publication No. 2006-22202
Patent Literature 7: Japanese Unexamined Patent Application Publication No. 2011-132265

Non Patent Literature

Non Patent Literature 1: Hayashi, T.; Maeda, K., Bull. Chem. Soc. Jpn. 1960, 33, 565-566
Non Patent Literature 2: Hartley, G. S., Nature 1937, 140, 281

SUMMARY OF INVENTION

Technical Problem

The security ink and the security mark described in Patent Literature 7 are visible only after color development of the photochromic compound by absorption of light, such as ultraviolet light, and before color quenching of the photochromic compound by cessation of the absorption of light, and are invisible during other periods of time and do not attract the attention of any person. Thus, high security performance is achieved.

The main object of the present invention is to provide a technique capable of achieving a method for authenticating a security mark containing a photochromic compound with higher security performance.

Solution of Problem

The present inventors have paid attention to the fact that the change in absorption spectrum or reflection spectrum of a photochromic compound in the process of a photochromic reaction (phototropy) is inherent in the structure of the compound, and have accomplished a technique for high-security authentication in the use of a time-dependent change in, for example, the absorption spectrum of a photochromic compound as information for security authentication by constructing the information through combining a plurality of photochromic compounds having different photochromic characteristics. The present invention accordingly provides the following method for authenticating a security mark and other techniques.

[1] A method for authenticating a security mark, comprising a process of irradiating a security mark containing a photochromic compound with excitation light and a process of acquiring first security information on a time-dependent change in the absorption spectrum and/or reflection spectrum of the security mark after the irradiation with excitation light;

[2] The method for authentication according to aspect [1], further comprising a process of checking the acquired first security information against previously acquired first security information on the security mark;

[3] The method for authentication according to aspect [2], wherein the acquired first security information is calibrated based on the temperature at the time of acquiring the first security information and is then checked against the previously acquired first security information on the security mark;

[4] The method for authentication according to one of aspects [1] to [3], wherein the security mark contains two or more photochromic compounds having different photochromic characteristics;

[5] The method for authentication according to aspect [4], wherein the two or more photochromic compounds contained in the security mark are different from one another in color development and/or in quenching rate after the color development in a photochromic reaction;

[6] The method for authentication according to aspect [5], wherein at least one of the photochromic compounds is quenched within one second from the color development in a photochromic reaction;

[7] The method for authentication according to aspect [6], wherein the security mark further contains a photochromic compound that is quenched after ten or more seconds from the color development in a photochromic reaction;

[8] The method for authentication according to one of aspects [1] to [7], wherein the security mark further contains a fluorescent substance, and the method further comprises a process of acquiring second security information on the spectrum of fluorescence emitted from the security mark and a process of checking the acquired second security information against previously acquired second security information on the security mark;

[9] The method for authentication according to one of aspects [1] to [8], wherein the excitation light includes ultraviolet light and/or light having a wavelength of 400 to 600 nm; and

[10] The method for authentication according to one of aspects [1] to [9], wherein the first security information is acquired by analyzing the time-resolved absorption spectrum and/or reflection spectrum.

[11] A device for authenticating a security mark, comprising an excitation light source for irradiating the security mark with excitation light including ultraviolet light and/or light having a wavelength of 400 to 600 nm; an observation light source for irradiating the security mark with visible and/or near-infrared light; a photodetector for detecting the visible and/or near-infrared light transmitted through or reflected by the security mark; and an analyzer for storing signals output from the photodetector as first security information on a time-dependent change in the absorption spectrum and/or reflection spectrum of the security mark after the irradiation with excitation light;

[12] The authentication device according to aspect [11] further comprising an output unit, wherein the analyzer holds previously acquired first security information on a security mark, checks the acquired first security information against the held first security information, and outputs the results of the check to the output unit; and [13] The authentication device according to aspect [12], wherein the analyzer holds calibration information regulating the relationship between the quenching rate and the temperature of the photochromic compound, calibrates the acquired first security information with the calibration information based on the temperature at the time of acquiring the first security information, and checks the calibrated first security information against the held first security information.

[14] An ink for a security mark, comprising two or more photochromic compounds having different photochromic characteristics;

[15] The ink for a security mark according to aspect [14], wherein the two or more photochromic compounds contained are different from one another in color development and/or in quenching rate after the color development in a photochromic reaction;

[16] The ink for a security mark according to aspect [15], wherein at least one of the photochromic compounds is quenched within one second from the color development in a photochromic reaction;

[17] The ink for a security mark according to aspect [16], further comprising a photochromic compound that is quenched after ten or more seconds from the color development in a photochromic reaction;

[18] A method for producing an ink for a security mark, comprising a step of mixing two or more photochromic compounds having different photochromic characteristics;

[19] The method according to aspect [18], wherein the two or more photochromic compounds mixed in the step are different from one another in color development and/or in quenching rate after the color development in a photochromic reaction;

[20] The method according to aspect [19], wherein at least one of the photochromic compounds is quenched within one second from the color development in a photochromic reaction; and

[21] The method according to aspect [20], wherein a photochromic compound that is quenched after ten or more seconds from the color development in a photochromic reaction is further mixed.

[22] A security mark comprising two or more photochromic compounds having different photochromic characteristics;

[23] The security mark according to aspect [22], wherein the two or more photochromic compounds are different from one another in color development and/or in quenching rate after the color development in a photochromic reaction;

[24] The security mark according to aspect [23], wherein at least one of the photochromic compounds is quenched within one second from the color development in a photochromic reaction;

[25] The security mark according to aspect [24] further comprising a photochromic compound that is quenched after ten or more seconds from the color development in a photochromic reaction;

[26] An article having the security mark according to one of aspects [22] to [25];

[27] A method for producing a security mark, comprising a step of mixing two or more photochromic compounds having different photochromic characteristics;

[28] The method according to aspect [27], wherein the two or more photochromic compounds mixed in the step are different from one another in color development and/or in quenching rate after the color development in a photochromic reaction;

[29] The method according to aspect [28], wherein at least one of the photochromic compounds is quenched within one second from the color development in a photochromic reaction; and

[30] The method according to aspect [29], wherein a photochromic compound that is quenched after ten or more seconds from the color development in a photochromic reaction is further mixed.

[31] A method for authenticating an article as an object to be authenticated, comprising a procedure of making a security mark in the object, the security mark containing two or more photochromic compounds different from one another in color development and/or in quenching rate after the color development in a photochromic reaction;

[32] A method for authenticating an article as an object to be authenticated, comprising a procedure of irradiating a security mark provided on the object with excitation light, the security mark containing two or more photochromic compounds different from one another in color development and/or in quenching rate after the color development in a photochromic reaction, and a procedure of acquiring first security information on a time-dependent change in the absorption spectrum and/or reflection spectrum of the security mark after the irradiation with excitation light;

[33] A method for authenticating an article as an object to be authenticated, comprising a procedure of checking first security information provided on the object against standard information, the first security information involving a time-dependent change in the absorption spectrum and/or reflection spectrum of a security mark that contains two or more photochromic compounds different from one another in color development and/or in quenching rate after the color development in a photochromic reaction; and

[34] The method of authentication according to one of aspects [31] to [33], wherein the object is selected from a financial security, a bank note, a credit card, a cash card, a passport, an identification card or document, a driver license, a postage stamp, a tax stamp, a passenger ticket, an admission ticket, a consumer good, and packing thereof.

Throughout the specification, the term "security mark" refers to information optically detectable by the method of authentication according to the present invention and includes information (security information) allowing the security mark to be distinguishable from other security marks. The term "security mark" encompasses a variety of photochromic compound-containing characters, symbols, figures, and combinations thereof.

The term "article" refers to an "object" provided with such a security mark mentioned above and can be "authenticated" by the method of authentication according to the present invention. The term "article" encompasses a variety of financial securities, bank notes (paper currencies), credit cards, cash cards, passports, identification cards and documents, driver licenses, postage stamps, tax stamps, passenger tickets, admission tickets, consumer goods, and packing thereof. A security mark attached to a single object or a group of objects to be authenticated includes information (security information) making the objects distinguishable from another single object or a group of objects, attached with another security mark, to be authenticated.

Advantageous Effects

The present invention provides a technique that can achieve higher security performance in a method for authenticating a security mark containing a photochromic compound.

DESCRIPTION OF EMBODIMENTS

Preferred embodiments for carrying out the present invention will now be described with reference to the drawings. The following embodiments are given for mere illustration of the present invention and should not be intended to limit the scope of the invention.

1. Method for Authenticating a Security Mark

A method for authenticating a security mark according to the present invention involves the following processes: (1) a process of irradiating a security mark containing a photochromic compound with excitation light (irradiation process); (2) a process of acquiring first security information on a time-dependent change in absorption spectrum and/or reflection spectrum of the security mark after the irradiation with excitation light (first information-acquiring process); and (3) a process of checking the acquired first security information against previously acquired first security information on a security mark (first checking process).

The method for authenticating a security mark according to the present invention may further involve the following processes: (4) a process of acquiring second security information on the spectrum of fluorescence emitted from the security mark (second information-acquiring process); and (5) a process of checking the acquired second security information against previously acquired second security information on a security mark (second checking process).

In the present invention, the term "first security information" refers to information on a time-dependent change in absorption spectrum and/or reflection spectrum of a security mark containing a photochromic compound and includes information on the absorption wavelength (or reflection wavelength) of the photochromic compound and/or the intensity of the absorption and information on the time. The term "first security information" may further include information on the temperature at the time of acquiring the information.

Figure 1:
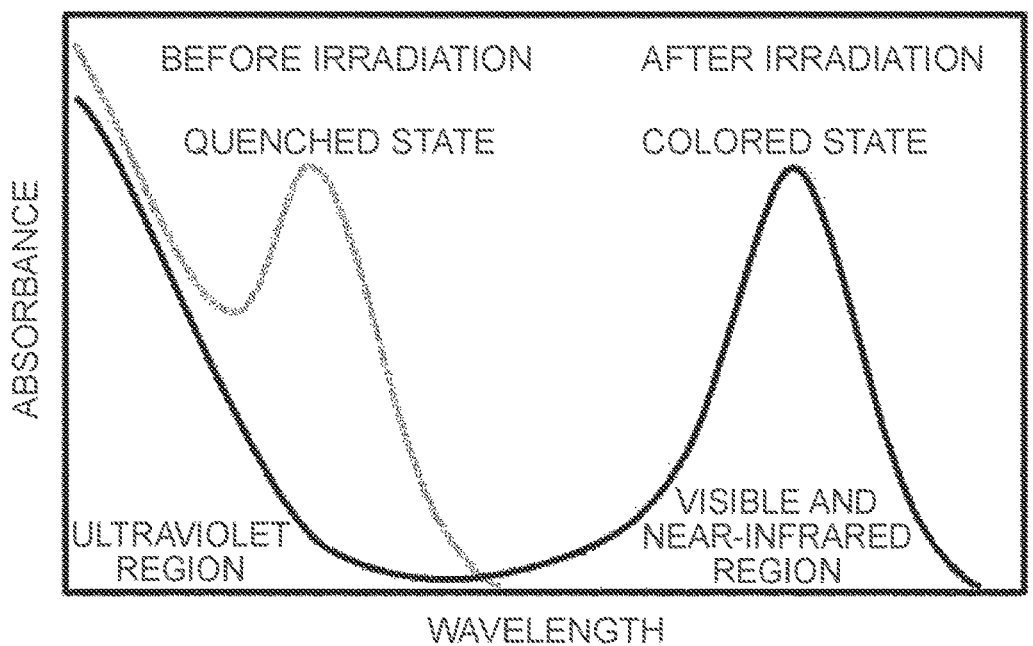
FIG. 1 is a graph illustrating changes in absorption spectrum by the photochromic reaction of a photochromic compound.
Figure 2:
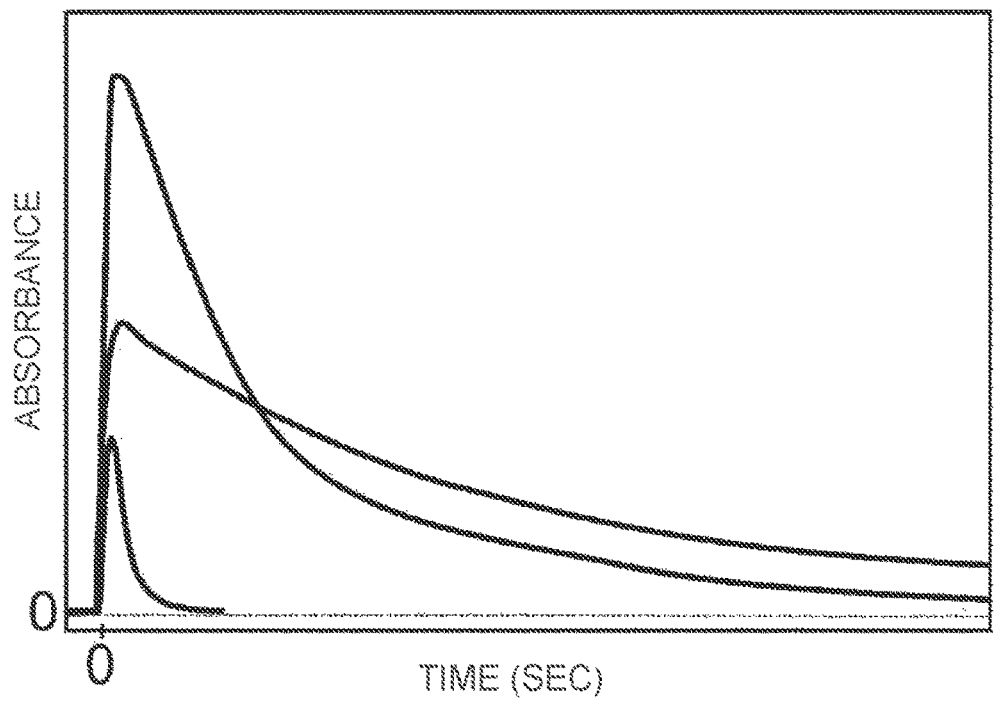
FIG. 2 is a graph illustrating time-dependent changes in absorbance during the quenching process of the colored forms of photochromic compounds.

The photochromic compound irradiated with excitation light varies the structure (isomerization) without changing the molecular weight, resulting in a change in the absorption spectrum. FIG. 1 shows an example change in absorption spectrum of a photochromic compound from a color-quenched state to a colored state by irradiation of the compound with excitation light. Before the irradiation with excitation light, the photochromic compound has an absorption spectrum showing no absorption in the visible and/or near-infrared region and is colorless (the absorption spectrum of "BEFORE IRRADIATION" in the drawing). The photochromic compound irradiated with excitation light causes color development and has an absorption spectrum showing absorption in the visible and/or near-infrared region (the absorption spectrum of "AFTER IRRADIATION" in the drawing). Cessation of the irradiation with excitation light causes color quenching of the photochromic compound and restores the absorption spectrum to the state before the irradiation with excitation light. Thus, the absorption spectrum of the photochromic compound reversibly changes between two different states in accordance with a photochromic reaction. FIG. 2 shows examples of time-dependent changes in absorbance at a specific wavelength of photochromic compounds irradiated with excitation light by cessation of the irradiation. Irradiation with excitation light (at 0 sec in the drawing) generates a colored form and immediately increases the absorbance at a specific wavelength (herein three wavelengths are shown) in visible and/or near-infrared region. Cessation of the irradiation with excitation light returns the colored form to a color-quenched form and gradually decreases the absorbance.

The method for authenticating a security mark according to the present invention uses information on such a time-dependent change in absorption spectrum and/or reflection spectrum of a photochromic compound as "first security information" including the wavelength and/or the intensity thereof and the time. Herein, a change in the light absorbed by a photochromic compound is accompanied by a correlative change in the transmitted complementary color light. Accordingly, in the "first security information" of the present invention, the "absorption spectrum" and the "transmission spectrum" of a security mark are synonymous with each other unless otherwise specified. Since a change in the "absorption spectrum" of a photochromic compound is accompanied by a correlative change in the "reflection spectrum", the "first security information" of the present invention includes not only information on a time-dependent change in the absorption spectrum (or transmission spectrum) of a security mark but also information on a time-dependent change in the reflection spectrum of the security mark. If the object provided with a security mark does not have optical transparency, information on the reflection spectrum of the security mark is preferably used as the first security information.

There are many photochromic compounds having different photochromic characteristics, i.e., color development and/or quenching rate after the color development in a photochromic reaction. In addition, a variety of photochromic compounds showing different color development and quenching rates can be designed by modifying the structures of known compounds. The first security information is inherent in the photochromic compound contained in a security mark and varies depending on the photochromic characteristics of the compound, which can be used for high-security authentication.

Furthermore, addition of two or more photochromic compounds different from one another in color development and/or in quenching rate after the color development in a photochromic reaction to the security mark can produce a numerous number of patterns of a time-dependent change (first security information) in the absorption spectrum and/or reflection spectrum of a security mark after absorption of excitation light.

Though compounds colored by absorption of excitation light have been described above as the photochromic compounds, the photochromic compound in the method for authenticating a security mark according to the present invention may show "reverse photochromism", i.e., color quenching by absorption of excitation light (see Journal of the American Chemical Society, 2013, 135, 3164-3172). That is, a reverse photochromic compound loses the absorbability in the visible and/or near-infrared region of the absorption spectrum by absorption of excitation light to cause color quenching and returns the original absorption spectrum by cessation of the absorption of light to cause color development. Information on a time-dependent change in the absorption spectrum of such a reverse photochromic compound can be also used in the "first security information".

In the present invention, the term "second security information" refers to information on the spectrum of fluorescence emitted from a security mark containing a photochromic compound and a fluorescent substance.

Since the fluorescence spectrum of a fluorescent substance is inherent in the substance, combined use of the second security information and the first security information can further enhance the security in authentication.

Each process of the method for authenticating a security mark according to the present invention will now be described in sequence.

[Irradiation Process]

The irradiation process involves irradiation of a security mark containing a photochromic compound with excitation light. The excitation light includes ultraviolet light and/or light having a wavelength of 400 to 600 nm. The method for authenticating a security mark according to the present invention may involve a process of producing the security mark as a previous stage to the irradiation process. The production process will be described in detail in the paragraphs of the method of producing an ink for a security mark and the method of producing a security mark according to the present invention.

The security mark may be irradiated with excitation light for any period of time, for example, about 10 to 200 milliseconds, required for color development of a photochromic compound. Although color quenching occurs in a reverse photochromic compound, the following description will be exemplified with a photochromic compound.

[First Information-Acquiring Process]

The first information-acquiring process acquires first security information on a time-dependent change in the absorption spectrum and/or reflection spectrum of a security mark irradiated with excitation light.

The first security information is acquired by irradiating the security mark, irradiated with excitation light, with visible and/or near-infrared light and detecting the transmitted or reflected visible and/or near-infrared light over time with a detector. The visible light may be white light.

The time of irradiation of the security mark with visible and/or near-infrared light may be appropriately determined depending on the time necessary for color quenching of the photochromic compound, for example, about 0.1 to 10 seconds. The first security information may be acquired simultaneously with the start of the irradiation with excitation light. In such a case, the security mark is irradiated with visible and/or near-infrared light and excitation light at the same time.

The first security information can be preferably acquired through measurement of the absorption wavelength (or reflection wavelength) and/or the absorbance of the colored form of a photochromic compound with a time-resolved absorption spectrum and/or reflection spectrum-measuring device, for example, with pulsed light from an ultraviolet LED (365 nm) as an excitation light source and with a white LED as a visible light source and/or a near-infrared LED as a near-infrared light source. Alternatively, a security mark authentication device according to the present invention described below can also be used as a simpler device for measurement.

In the measurement of the absorption spectrum and/or the reflection spectrum of a security mark, the baseline is desirably corrected. In detail, the baseline is desirably corrected by subtracting the background value, i.e., the absorption spectrum and/or the reflection spectrum acquired by irradiation with only white light, from the spectrum acquired by irradiation with excitation light.

Figure 3:
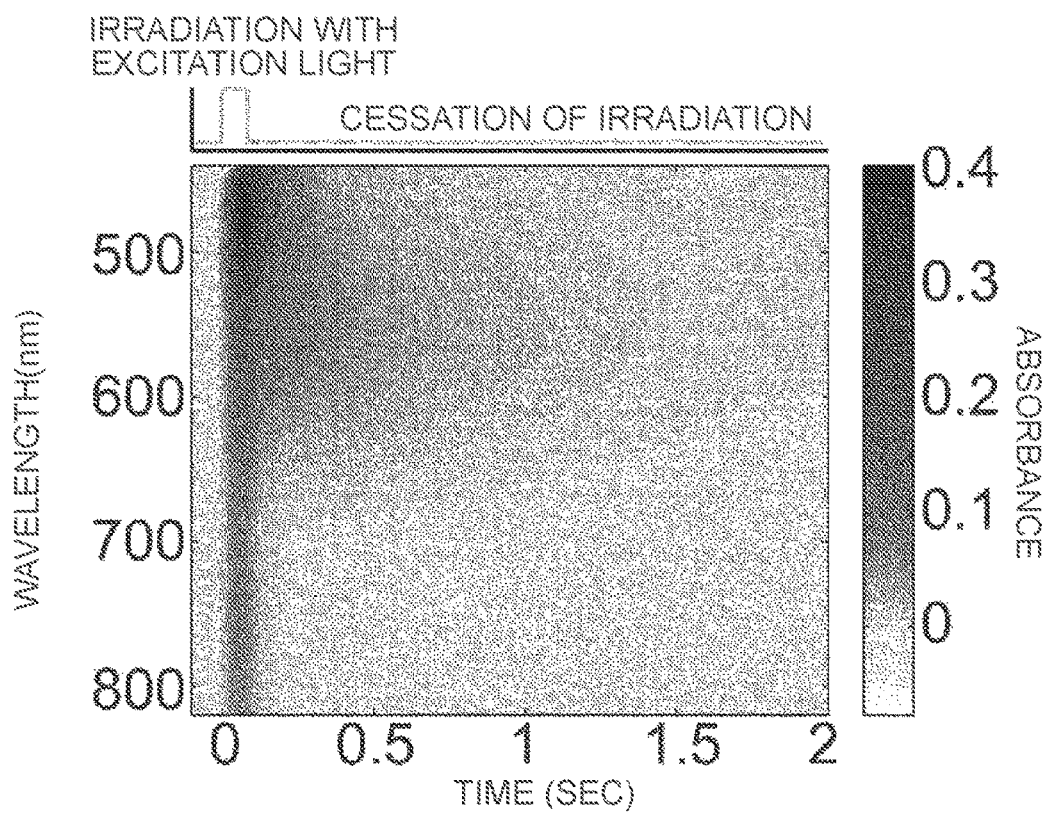
FIG. 3 is a diagram illustrating first security information (two dimensional absorption spectrum of wavelength versus time) acquired from a security mark containing three photochromic compounds A, B, and C having different photochromic characteristics.
Figure 4:
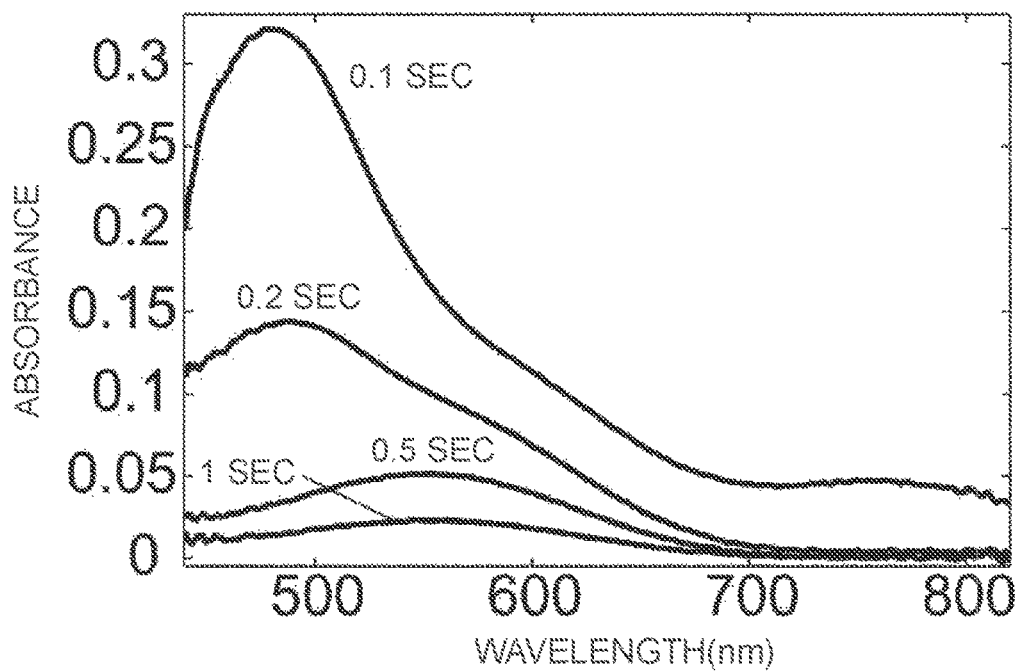
FIG. 4 is a graph illustrating first security information (absorption spectrum) acquired from a security mark containing photochromic compounds A, B, and C.
Figure 5:
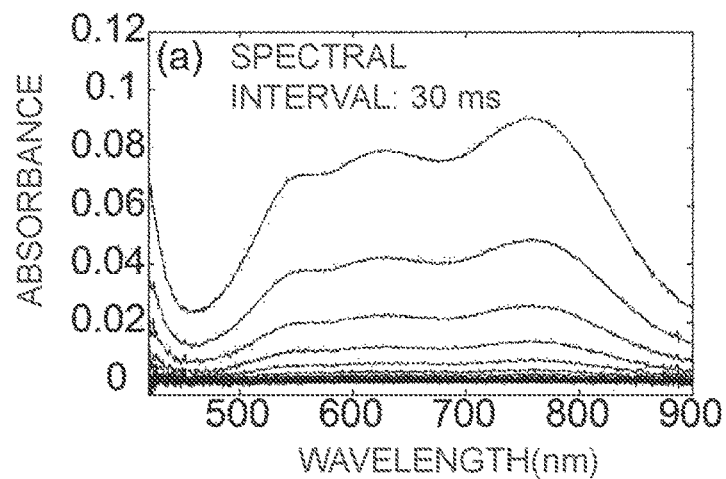
FIG. 5 includes graphs illustrating time-dependent changes in absorption spectrum during the quenching process of the colored forms of (a) photochromic compound A, (b) photochromic compound B, and (c) photochromic compound C.
Figure 5:
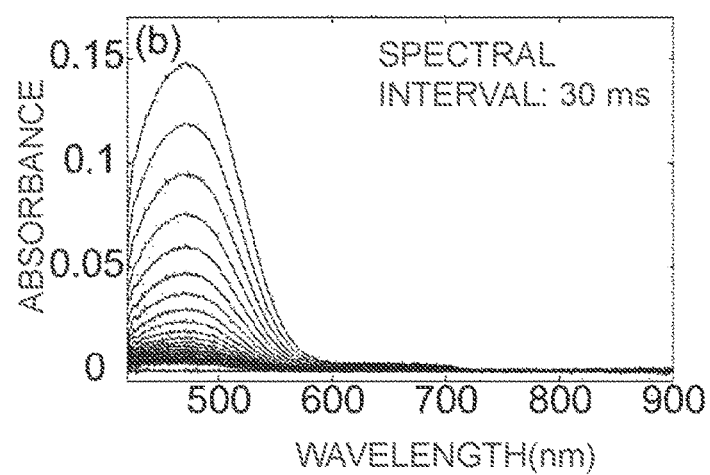
Figure 5:
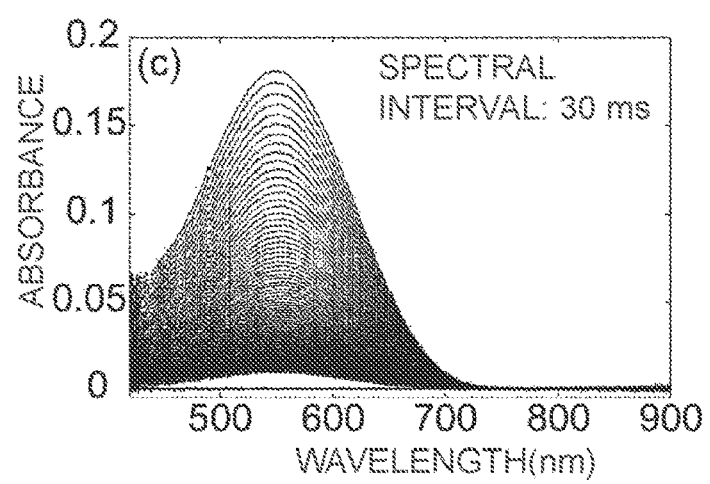

FIGS. 3 and 4 illustrate examples of acquired first security information. FIG. 3 is two-dimensional illustration of an absorption spectrum of the absorption wavelength on the vertical axis versus the time on the horizontal axis. FIG. 4 shows the absorption spectrum at each acquisition time of data where the vertical axis indicates the absorbance and the horizontal axis the absorption wavelength. FIGS. 3 and 4 show the first security information on a security mark containing three photochromic compounds A, B, and C having different photochromic characteristics. FIG. 5 shows time-dependent changes in the absorption spectra of the colored forms of photochromic compounds A, B, and C, generated by absorption of excitation light. The vertical axis indicates the absorbance, and the horizontal axis indicates the absorption wavelength.

The photochromic reaction causes absorption by photochromic compound A over the visible to near-infrared region, in particular, strong absorption around 780 nm, and causes absorption by photochromic compound B around 470 nm and by photochromic compound C around 550 nm. The half-lives of the colored forms at room temperature are about 30 milliseconds, about 100 milliseconds, and about 1 second in compound A, compound B, and compound C, respectively.

Figure 6:
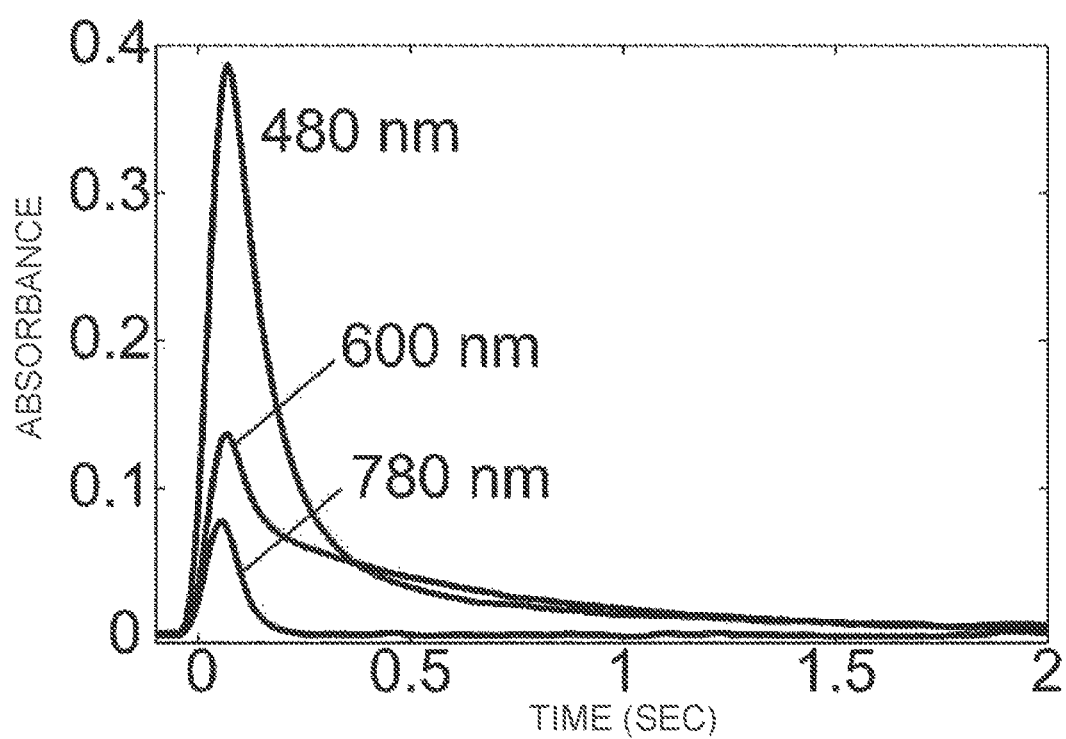
FIG. 6 is a graph illustrating time-dependent changes in absorbance at three different wavelengths during the quenching process of the colored forms of photochromic compounds A, B, and C.

The acquired first security information on the security mark includes characteristic changes at wavelengths of around 470 nm, 550 nm, and 780 nm caused by changes in the absorption spectra of photochromic compounds A, B, and C (see FIGS. 4 and 5). FIG. 6 illustrates the time-dependent changes in absorbance at wavelengths of near 480 nm, 600 nm, and 780 nm extracted from the first security information on the security mark. FIG. 6 illustrates the absorbance on the vertical axis and the time on the horizontal axis.

In the first information-acquiring process, the first security information may be acquired by spectral measurement over the whole visible and/or near-infrared light region, as shown in FIGS. 3 and 4 or by measurement of absorbance at a specific wavelength (preferably at multiple wavelengths), as shown in FIG. 6, for increasing the throughput rate.

[First Checking Process]

The first checking process checks the first security information acquired in the first information-acquiring process against previously acquired first security information on a security mark.

Specifically, first security information (hereinafter, also referred to as "standard information") on a security mark containing a specific photochromic compound is acquired in advance. First security information (hereinafter, also referred to as "inquiry information") on a security mark to be authenticated acquired in the first information-acquiring process is then checked against the standard information for security authentication based on the concordance rate therebetween. The standard information may be known information, instead of that measured in advance.

The inquiry information can be checked against standard information by comparing two dimensional absorption spectra of wavelength versus time including information on absorption wavelength, time, and absorbance or absorption spectra as shown in FIGS. 3 and 4. The comparison may be performed over the two dimensional absorption spectra of wavelength versus time or absorption spectra or with partially selected and extracted characteristic amounts. For example, the overall spectra can be compared by known analysis using fitting curves by a least squares method. The characteristic amounts may be, for example, the slopes of absorbance decay curves or the absorbance peak ratios at a plurality of wavelengths in the colored states. For example, in the case of a security mark containing photochromic compounds A, B, and C, the characteristic amounts may be the peak ratio appearing at wavelengths of around 470 nm, 550 nm, and 780 nm due to the photochromic characteristics of photochromic compounds A, B, and C.

A simple authentication algorithm in the case of a security mark containing photochromic compounds A, B, and C is as follows: The following four conditions 1 to 4 are established based on standard information previously acquired on the security mark containing photochromic compounds A, B, and C. Inquiry information is determined to be consistent with the standard information if the inquiry information satisfies all of conditions 1 to 4, whereas the inquiry information is determined to be inconsistent with the standard information if any one of the conditions is not satisfied.

Condition 1: absorption spectra corresponding to the colored states of compounds A, B, and C are detected during irradiation with excitation light; Condition 2: absorption around 780 nm is observed from immediately after the irradiation with excitation light until 0.1 seconds after the irradiation (see FIG. 4); Condition 3: an absorption peak around 470 nm is observed at 0.2 seconds after the irradiation with excitation light; and Condition 4: an absorption peak around 550 nm is observed at 0.5 seconds after the irradiation with excitation light. A photochromic reaction causes absorption in photochromic compound A around 780 nm, absorption in photochromic compound B around 470 nm, and absorption in photochromic compound C around 550 nm. The quenching rate decreases in order of compounds A, B, and C. The half-lives of compounds A, B, and C at room temperature are respectively about 30 milliseconds, about 100 milliseconds, and about 1 second.

The quenching rate of a photochromic compound varies depending on temperature. Accordingly, in this process, the inquiry information is desirably calibrated with the temperature at the time of the acquisition and is then checked against standard information. The calibration with temperature can be performed by a usual procedure with a calibration curve regulating the relationship between the temperature and the quenching rate. The calibration curve may be previously acquired or may be selected from the library.

If the reflection spectrum of a security mark is used as the first security information, the spectrum of a reflection spectrum light source should be known. Accordingly, in this process, information on the spectrum of a reflection spectrum light source may be referred for checking inquiry information against standard information. The use of information on the spectrum of a reflection spectrum light source in authentication further enhances the security performance.

[Second Information-Acquiring Process]

In the method for authenticating a security mark according to the present invention, the security mark may contain a fluorescent substance in addition to photochromic compounds. In such a case, second information-acquiring process is carried out to acquire second security information on the spectrum of fluorescence emitted from the security mark. The fluorescent substance may be any known compound.

The second security information is acquired by irradiating the security mark with excitation light and detecting the fluorescence emitted from the security mark with a detector. The excitation light for exciting the fluorescent substance may be the same as or different from the excitation light for exciting photochromic compounds. The excitation light for the fluorescent substance is preferably ultraviolet light.

[Second Checking Process]

The second checking process checks the acquired second security information against previously acquired second security information on a security mark.

In detail, second security information (hereinafter, also referred to as "standard information (fluorescence)") on a security mark containing a specific fluorescent substance is acquired in advance. Second security information (hereinafter, also referred to as "inquiry information (fluorescence)") on a security mark to be authenticated acquired in the second information-acquiring process is checked against the standard information (fluorescence) for security authentication based on the concordance rate therebetween. The standard information (fluorescence) may be known information, instead of that measured in advance.

2. Security Mark Authentication Device

Figure 7:
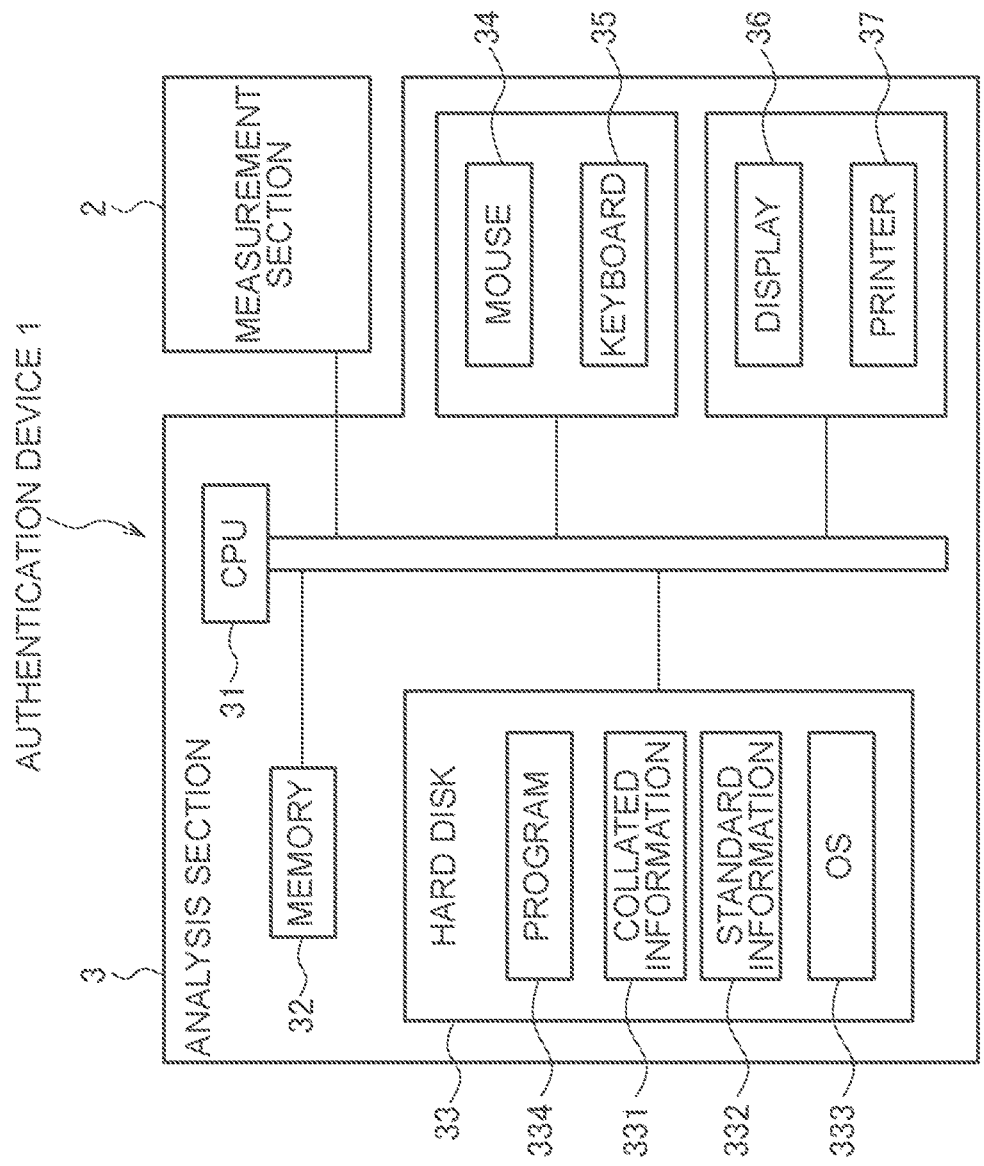
FIG. 7 is a block diagram illustrating a structure of a device for authenticating a security mark according to the present invention.
Figure 8:
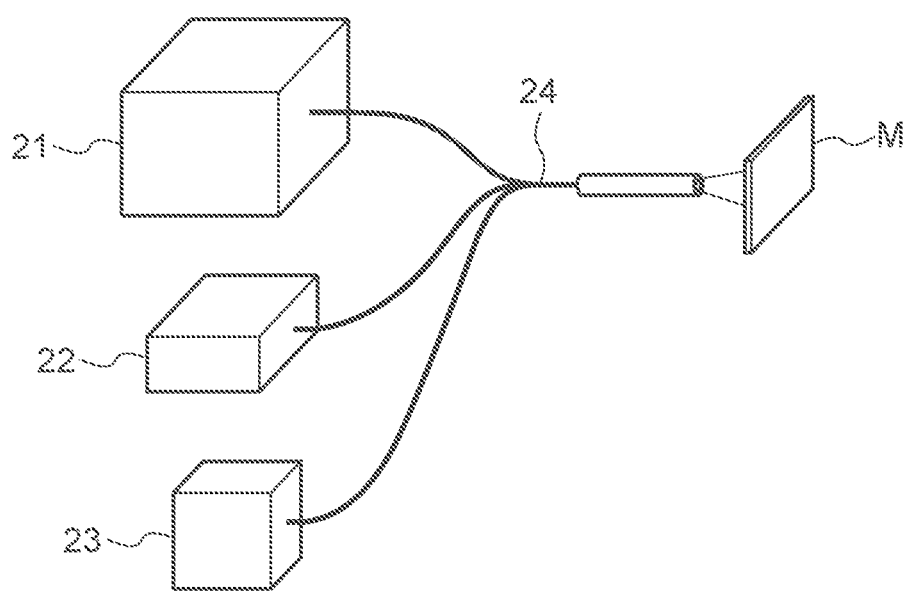
FIG. 8 is a schematic diagram illustrating a structure of the measurement unit of a device for authenticating a security mark according to the present invention.

An authentication device that can be used in the method for authenticating a security mark according to the present invention will now be described. FIGS. 7 and 8 illustrate the structure of the device for authenticating a security mark according to the present invention.

The authentication device 1 includes a measurement unit 2 and an analyzer 3. The measurement unit 2 carries out the "irradiation process" and the "first information-acquiring process" of the method for authenticating a security mark and optionally carried out the "second information-acquiring process". The analyzer 3 carries out the "first checking process" of the method and optionally carried out the "second checking process".

[Measurement Unit]

The measurement unit 2 includes an excitation light source 21 irradiating a security mark M with excitation light including ultraviolet light and/or light having a wavelength of 400 to 600 nm and an observation light source 22 irradiating the security mark M with visible and/or near-infrared light (see FIG. 8). The measurement unit 2 also includes a photodetector 23 detecting visible and/or near-infrared light transmitted through or reflected by the security mark M.

Excitation light emitted from the excitation light source 21 and visible and/or near-infrared light emitted from the observation light source 22 are guided to two optical fibers of a three-branch optical fiber bundle 24 and then radiated to the security mark M. A cover blocking external light from the outside is preferably disposed between the security mark M and the output end of the three-branch optical fiber bundle 24 for excitation light and visible and/or near-infrared light. Alternatively, the security mark M may be directly irradiated with excitation light and visible and/or near-infrared light, without the optical fibers.

The security mark M is irradiated with excitation light for a time necessary for excitation of the photochromic compound. Such a time is, for example, about 10 to 200 milliseconds. The time of irradiation of the security mark M with visible and/or near-infrared light may be appropriately determined depending on the quenching time of the photochromic compound and is, for example, about 0.1 to 10 seconds.

The security mark M is irradiated with visible and/or near-infrared light immediately after the irradiation with excitation light or at the same time with the irradiation with excitation light, as necessary. The visible and/or near-infrared light transmitted through or reflected by the security mark M is collected by the last optical fiber of the three-branch optical fiber bundle 24 and is detected with the photodetector 23. The transmitted or reflected light may be directly detected with the detector, without the optical fiber.

When both the absorption spectrum and the reflection spectrum of the security mark M are detected, an observation light source 22 and a photodetector 23 are provided for the absorption spectrum, and another observation light source 22 and another photodetector 23 are provided for the reflection spectrum. When the security mark M contains a fluorescent substance, an excitation light source (not shown) and a photodetector (not shown) for detecting the fluorescence spectrum of the security mark M may be further provided.

The excitation light source 21 and the observation light source 22 may be respectively an ultraviolet LED and a white LED. The photodetector 23 may include a photodiode array in combination with a spectrometer. A combination of an inexpensive photodiode and a color filter may also be used for detection of only a specific wavelength. The measurement unit 2 may be composed of a known time-resolved absorption spectrophotometer and/or reflection spectrophotometer.

[Analyzer]

The analyzer 3 includes a CPU 31, a memory 32, a hard disk 33, an input unit including a mouse 34 and a keyboard 35, and an output unit including a display 36 and a printer 37. The analyzer 3 can be composed of a general-purpose computer and a program.

The light transmitted through and/or reflected by the security mark M detected by the measurement unit 2 and optional fluorescent light are converted into electrical signals. The electrical signals are stored in the hard disk 33 of the analyzer 3 as first security information (inquiry information) and optional second security information (inquiry information (fluorescence)) (see reference number 331 in FIG. 7).

The hard disk 33 holds previously acquired first security information (standard information) and optional second previously acquired standard information (standard information (fluorescence)) on the security mark M (see reference number 332). In addition, the hard disk 33 stores an OS 333 and a program 334 for checking the inquiry information 331 and the standard information 332.

The analyzer 3 checks the inquiry information 331 against the standard information 332 with the OS 333 and the program 334 and outputs the results to the output unit including the display 36 and the printer 37. The check of the inquiry information 331 against the standard information 332 can be carried out as above-described for the first checking process and the second checking process. The inquiry information is calibrated with temperature with reference to the calibration information stored in the hard disk 33 and regulating the relationship between the temperature and the quenching rate. If the reflection spectrum of a security mark M is used as the first security information, the spectrum of a reflection spectrum light source should be known. Accordingly, the hard disk 33 also stores information on the spectrum of the light source.

3. Method of producing security mark
[Ink for Security Mark]

The ink for a security mark according to the present invention contains two or more photochromic compounds having different photochromic characteristics, more specifically, two or more photochromic compounds different from one another in color development and/or in quenching rate after the color development in a photochromic reaction.

Information on a time-dependent change in absorption spectrum and/or reflection spectrum of a photochromic compound and including the wavelength and/or the intensity thereof and the time can be used as information having high security, as described above. Accordingly, the photochromic compound is useful in an ink for a security mark.

Furthermore, addition of two or more photochromic compounds different from one another in color development and/or in quenching rate after the color development in a photochromic reaction to the ink for a security mark can produce a numerous number of patterns of a time-dependent change in the absorption spectrum and/or reflection spectrum after irradiation with excitation light, as described above. The ink for a security mark may contain any number of photochromic compounds, and the number is preferably about 2 to 20, more preferably about 3 to 10, in view of an improvement in security and cost.

The photochromic compound used in the present invention may be a known compound, such as the above-mentioned diarylethene (Patent Literature 1), spiropyran (Patent Literature 2), hexaarylbiimidazole (Non Patent Literature 1), or azobenzene (Non Patent Literature 2) compound.

Further preferred examples of the photochromic compound include compounds having a shorter induction time for a photochromic reaction. The use of a compound causing a rapid photochromic reaction shortens the time for measuring the absorption spectrum and/or reflection spectrum of the photochromic compound, resulting in an increase in the throughput rate of the authentication procedure. Examples of such photochromic compounds (rapid reversible photochromic compounds) include bisimidazole compounds described in Patent Literature 7, which is an application by the present inventors, Japanese Patent No. 464376, and Japanese Unexamined Patent Application Publication Nos. 2011-122089, 2011-144289, and 2012-251097. These compounds are rapidly quenched after cessation of the irradiation with excitation light. The time necessary for the quenching is several tens of nanoseconds to several seconds, preferably 1 microsecond to 1 second, and more preferably 10 to 100 microseconds.

The ink for a security mark according to the present invention may contain a compound having a considerably long quenching time, in addition to the compound having a short quenching time. An ink for a security mark purposely containing a compound having a long quenching time, for example, a compound having a quenching time of several seconds, preferably ten or more seconds, after the color development in a photochromic reaction allows the photochromic reaction of the ink to be visually recognized by an observer, resulting in visual security.

In the security authentication, only a change in the absorption spectrum and/or reflection spectrum of a rapid reversible photochromic compound may be used as the first security information. In addition to such a change, a change in the absorption spectrum and/or reflection spectrum of a photochromic compound having a long color quenching time may also be used as the first security information. In order to increase the throughput rate, the authentication is preferably carried out with only information acquired from a rapid reversible photochromic compound. In such a case, a change in the color of a compound having a long color quenching time appeals visual security and also functions so as to hide a change in color of a rapid reversible photochromic compound actually used in authentication, resulting in an increase in the confidentiality of authentication information and an improvement in the security.

The ink for a security mark according to the present invention can be produced by dissolving or dispersing two or more photochromic compounds having different photochromic characteristics in a common ink solvent.

Unlimited examples of the solvent include benzene, toluene, chloroform, methylene chloride, methanol, 2-propanol, 2-methoxyethanol, acetone, methyl ethyl ketone, and mixtures thereof. The ink for a security mark may contain miscellaneous additives.

The solvent may contain polymers, such as resins. Unlimited examples of the polymer include poly(methyl methacrylate) (PMMA), polystyrene, polyimides, polycarbonates, polyethylene, poly(ethylene terephthalate), poly(vinyl chloride), poly(vinylidene chloride), poly(lactic acid), polypropylene, polyamides, polycarbonates, polytetrafluoroethylene, polyurethanes, polyesters, ABS resins, epoxy resins, and polyacetal. These polymers may be used alone or in combination. The solvent containing a polymer may be prepared by dissolving the polymer in the solvent or by dissolving a monomer that can form the polymer through, for example, polymerization in the solvent.

[Security Mark]

The security mark according to the present invention contains two or more photochromic compounds having different photochromic characteristics, more specifically, two or more photochromic compounds different from one another in color development and/or in quenching rate after the color development in a photochromic reaction. The security mark according to the present invention can be formed by coating or printing the ink for a security mark on an object to be authenticated.

Unlimited examples of the article or object include financial securities, bank notes (paper currencies), credit cards, cash cards, passports, identification cards and documents, driver licenses, postage stamps, tax stamps, passenger tickets, admission tickets, consumer goods, and packing thereof. Examples of the financial securities include national bonds, municipal bonds, corporate bonds, investment securities, stock certificates, entrusted securities, and mortgage securities. Examples of the consumer goods include industrial products, farm and marine products, foods and drinks, and pharmaceutical products. The industrial products are not only finished products but also parts (in particular, electronic parts, such as semiconductor elements) for assembling finished products.

The first security information and the second security information held by the security mark according to the present invention may include records of, for example, the identity (authenticity), manufacturer, publisher, production site, issuing site, production date, issued date, holder, user, distribution channel, trading history, and history of use of the article. The security mark according to the present invention can be used for checking and authenticating such information.

Preferred first security information is information on a time-dependent change in the absorption spectrum and/or transmission spectrum of a security mark for an object to be authenticated having optical transparency, or information on a time-dependent change in the reflection spectrum for an object not having optical transparency.

The security mark may be formed on an object by coating, for example, brush coating, spray coating, immersion coating, electrostatic coating, or roller coating. Alternatively, the security mark may be formed on an object by printing, for example, intaglio printing, relief printing, lithographic printing, screen printing, offset printing, or ink-jet printing.

The security mark may be, for example, a character and/or a figure. If the security mark is a figure, it may be a two-dimensional image, such as a QR code (registered trademark). The mark may be, for example, formed by coating or printing in the two-dimensional shape while varying the two-dimensional distribution of the types and the densities of photochromic compounds. As a result, more complicated and high-security authentication information can be constructed by combining the positional information in the mark and the first security information acquired at the position.

The security mark can also be used for detecting tamper opening by attaching the mark to the opening port of an article as an object to be authenticated or its packing such that the mark is broken by opening operation. For example, if the security mark contains photochromic compounds so as to vary the two-dimensional distribution of the types and the densities of the photochromic compounds in a two-dimensional shape as mentioned above, breakage of the mark changes the positional information in the mark and the first security information acquired at the position to determine the opening.

INDUSTRIAL APPLICABILITY

The method for authenticating a security mark with a photochromic compound and other techniques according to the present invention can be applied to authentication of financial securities, bank notes (paper currencies), credit cards, cash cards, passports, identification cards and documents, driver licenses, postage stamps, tax stamps, passenger tickets, admission tickets, and consumer goods and are useful for finding and preventing forgery, unauthorized duplicating, replacement, and confusion thereof.

REFERENCE SIGNS LIST

1: authentication device, 2: measurement unit, 21: excitation light source, 22: observation light source, 23: photodetector, 24: three-branch optical fiber bundle, 3: analyzer, 331: inquiry information, 332: standard information

What is claimed is:

1. A method for authenticating a security mark, comprising:
    irradiating a security mark containing at least one first photochromic compound that is quenched within one second from the color development in a photochromic reaction, and at least one second photochromic compound that is quenched after ten or more seconds from the color development in a photochromic reaction, with excitation light, wherein the first and second photochromic compounds are spatially coincident and each exhibit a time-dependent change in an absorption wavelength and/or a reflection wavelength upon irradiation; and
    acquiring first security information corresponding to the time-dependent change in the absorption wavelength and/or reflection wavelength of the security mark after the irradiation with excitation light, wherein the first security information comprises information on the time-dependent change in absorption wavelength or reflection wavelength of the first photochromic compound, wherein information on the time-dependent change in absorption wavelength or reflection wavelength solely of the first photochromic compound is used as the first security information and wherein the time-dependent change in the absorption wavelength or reflection wavelength of the second photochromic compound functions so as to hide the time-dependent change in absorption wavelength or reflection wavelength of the first photochromic compound from an observer.

2. The method for authenticating a security mark according to claim 1, further comprising a process of checking the acquired first security information against security information previously acquired from the security mark, wherein the acquired first security information is checked against the previously acquired security information by comparing two dimensional absorption spectra of wavelength versus time including information on absorption wavelength, time, and absorbance or absorption spectra.

3. The method for authenticating a security mark according to claim 2, wherein
    the acquired first security information is calibrated based on the temperature at the time of acquiring the first security information and is then checked against the previously acquired security information on the security mark.

4. The method for authenticating a security mark according to one of claim 3, wherein the security mark further contains a fluorescent substance, and the method further comprises a process of acquiring second security information on the spectrum of fluorescence emitted from the security mark and a process of checking the acquired second security information against the previously acquired security information.

5. A measuring device comprising:
    an excitation light source for irradiating a security mark with excitation light comprising ultraviolet light and/or light having a wavelength of 400 to 600 nm, the security mark comprising at least one first photochromic compound that is quenched within one second from the color development in a photochromic reaction, and at least one second photochromic compound that is quenched after ten or more seconds from the color development in a photochromic reaction, wherein the first and second photochromic compounds are spatially coincident and each exhibit a time-dependent change in an absorption wavelength and/or a reflection wavelength upon irradiation by the excitation light source;
    an observation light source for irradiating the security mark with visible and/or near-infrared light; and
    a photodetector for detecting the visible and/or near-infrared light transmitted through or reflected by the security mark and generate therefrom an electrical signal output indicative of the time-dependent change in an absorption spectrum and/or a reflection spectrum of the first photochromic compound; and
    an analyzer configured to receive the electrical signal output from the photodetector and to store the electrical signal output as first security information indicative of the time-dependent change in the absorption spectrum and/or reflection spectrum of the security mark after the irradiation with excitation light, wherein the analyzer processes information on the time-dependent change in absorption wavelength or reflection wavelength solely of the first photochromic compound as the first security information, and wherein the time-dependent change in the absorption wavelength or reflection wavelength of the second photochromic compound functions so as to hide the time-dependent change in absorption wavelength or reflection wavelength of the first photochromic compound from an observer.

6. The authentication device comprising the measuring device according to claim 5, wherein the analyzer is further configured to compare for concordance the first security information against stored security information previously acquired from the security mark.

7. The authentication device according to claim 6, wherein the analyzer stores calibration information that correlates a relationship between quenching rate of the photochromic compound and temperature of the photochromic compound, and wherein the analyzer calibrates the acquired first security information with the calibration information based on a temperature measured at the time of acquiring the first security information prior to comparing the first security information against the stored security information.

\* \* \* \* \*